United States Patent [19]
Schiff

[11] Patent Number: 4,552,127
[45] Date of Patent: Nov. 12, 1985

[54] PERCUTANEOUS INTRA-AORTIC BALLOON HAVING AN EKG ELECTRODE AND A TWISTING STYLET FOR COUPLING THE EKG ELECTRODE TO MONITORING AND/OR PACING INSTRUMENTATION EXTERNAL TO THE BODY

[76] Inventor: Peter Schiff, Rte. 7, Cookeville, Tenn. 38501

[21] Appl. No.: 481,323

[22] Filed: Apr. 1, 1983

[51] Int. Cl.⁴ .................. A61B 5/04; A61M 25/00
[52] U.S. Cl. .................. 128/1 D; 128/344; 128/642; 604/96
[58] Field of Search .............. 128/642, 784–786, 128/419 P, 1 D, 344, 715; 604/96

[56] References Cited

U.S. PATENT DOCUMENTS

| | | | |
|---|---|---|---|
| 3,568,660 | 3/1971 | Crites et al. | 128/786 |
| 3,707,960 | 1/1973 | Freed | 128/642 |
| 3,837,347 | 9/1974 | Tower | 128/785 |
| 4,073,287 | 2/1978 | Bradley et al. | 128/642 |
| 4,106,512 | 8/1978 | Bisping | 128/785 |
| 4,349,031 | 9/1982 | Perlin | 128/715 X |
| 4,362,150 | 12/1982 | Lombardi, Jr. et al. | 128/1 D |
| 4,362,166 | 12/1982 | Furler et al. | 128/715 |

FOREIGN PATENT DOCUMENTS 8002231 10/1980 World Intel. Prop. Org. .... 128/786
8102110 8/1981 World Intel. Prop. Org. .... 128/344

Primary Examiner—Lee S. Cohen
Attorney, Agent, or Firm—Louis Weinstein

[57] ABSTRACT

An intra-aortic balloon adapted for percutaneous insertion and having a stylet whose distal end is coupled to an electrode arranged in the tip of the balloon. The stylet extends rearwardly through the balloon and catheter tube and is accessible at a location external to the body for coupling to an instrument such as a cathode ray tube establishing an electrical path from the electrode to the instrument. The stylet thus performs the dual function of providing twisting and untwisting of the balloon and providing an electrical path from the EKG electrode to the exterior of the body. The electrode may be arranged adjacent to either the distal or the proximal end of the balloon. An electrode arranged adjacent to the proximal end of the balloon may be coupled to a conductor embedded within the wall of the catheter tube, enabling the intra-aortic balloon to be provided with electrodes arranged adjacent to both the distal and proximal ends of the balloon.

21 Claims, 12 Drawing Figures

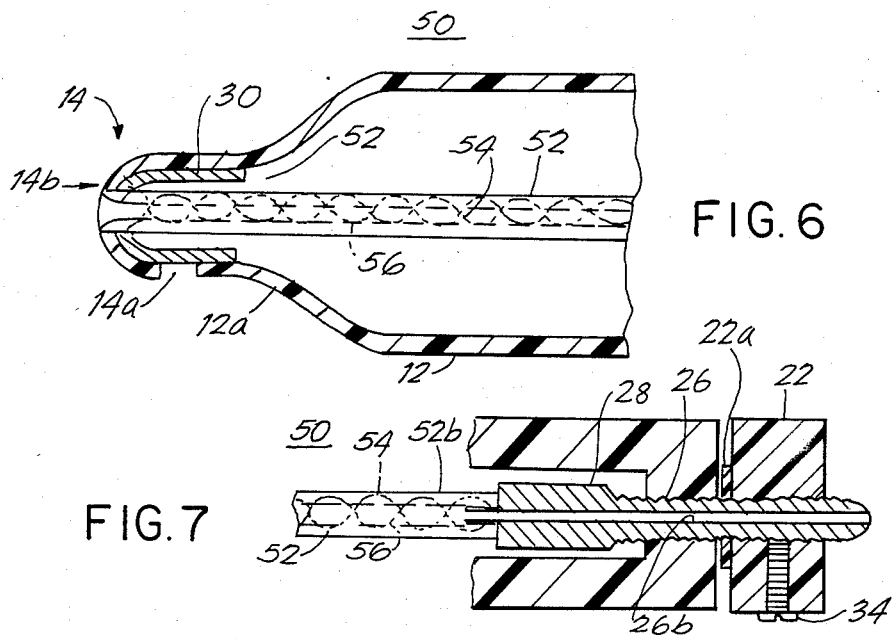
FIG. 6
FIG. 7
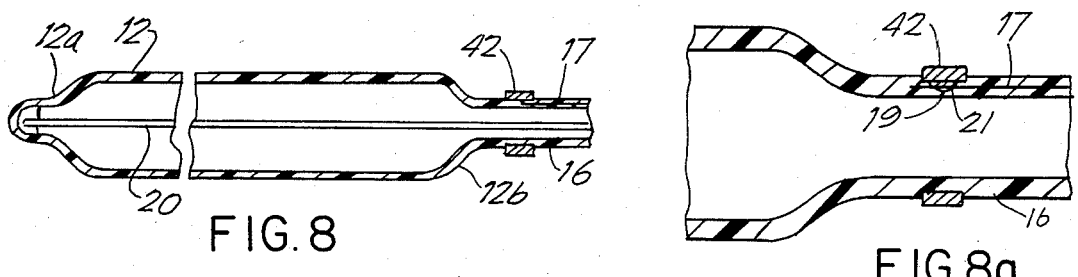
FIG. 8
FIG. 8a
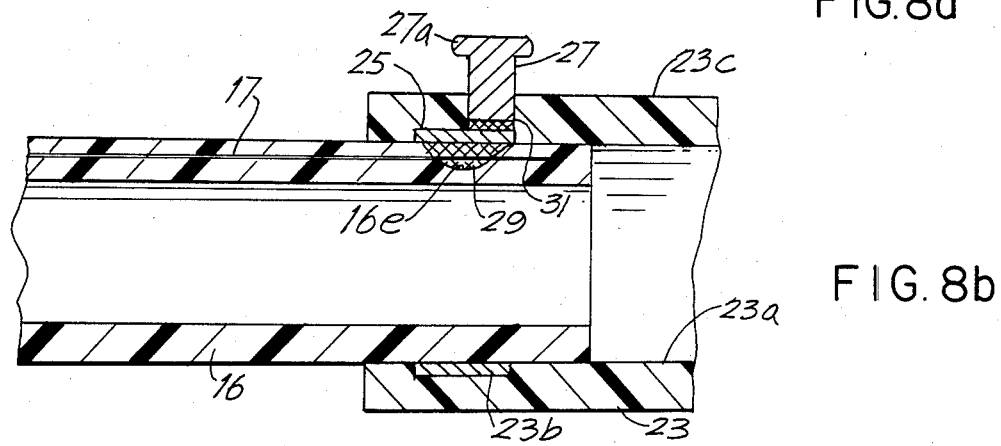
FIG. 8b
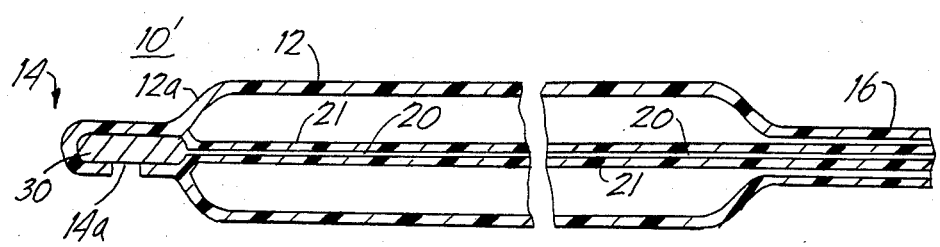
FIG. 9

PERCUTANEOUS INTRA-AORTIC BALLOON HAVING AN EKG ELECTRODE AND A TWISTING STYLET FOR COUPLING THE EKG ELECTRODE TO MONITORING AND/OR PACING INSTRUMENTATION EXTERNAL TO THE BODY

FIELD OF THE INVENTION

The present invention relates to intra-aortic balloons and more particularly to intra-aortic balloons adapted for percutaneous insertion and having a twisting stylet which provides the additional function of establishing an electrical path from the electrode to instrumentation external to the body.

BACKGROUND OF THE INVENTION

Intra-aortic balloons (IAB's) are utilized to assist a weakened heart in the blood pumping function. The intra-aortic balloon is inserted into the body through the femoral artery for placement in the vicinity of the aortic arch. Since the femoral artery has a narrow diameter, it is important to provide a balloon having the smallest possible profile to facilitate entry and placement of the IAB. This has been accomplished through the development of the twistable balloon such as, for example, that described in copending application Ser. No.: 253,680 filed Apr. 13, 1981; which has matured into U.S. Pat. No. 4,422,477, dated Dec. 27, 1983. The intra-aortic balloon described in the abovementioned copending application is provided with an elongated stylet and operating means positioned external to the body for twisting the stylet in order to twist the balloon and cause it to be wrapped about the stylet, thereby significantly reducing the profile of the balloon and greatly facilitating its insertion into the femoral artery. Upon insertion and proper placement of the balloon, the operating means is rotated in the reverse direction causing the balloon to be untwisted and thereby placed in readiness for a balloon pumping operation.

The IAB is operated in synchronism with the operation of the weakened heart. In order to synchronize the operation of the IAB with the heart, it is conventional to employ an EKG signal which is derived by coupling a pair of electrodes, typically to the chest of the patient, which electrodes are coupled through conductors to an instrument which utilizes the R wave of an EKG for triggering balloon pumping. Instruments of this type also are provided with visual display means which make it possible to view the EKG signal and the balloon pumping signal to be assured of proper synchronism of the IAB with the heart and to monitor the progress of the balloon pumping operation.

The electrodes are typically coupled to the chest area of the patient. The electrical interface between the patient's body and the electrodes is of high resistivity, causing significant signal loss and erroneous signals through the interface. This decreases the integrity of the signal, and this condition is compounded by a weakened heart condition resulting in an EKG signal which is frequently insufficient for purposes of monitoring the heart and operating the IAB in synchronism with the pumping heart.

In addition, the "skin" electrodes are subject to erroneous signals complexes due to movement by the patient or disturbance of the electrodes by the medical procedure. These "false" signals may be incorrectly interpreted as "R-waves" and result in incorrect and harmful timing of the balloon.

BRIEF DESCRIPTION OF THE INVENTION

The present invention is characterized by comprising an IAB which utilizes a stylet having an operating member for twisting the balloon to reduce the outer diameter of the balloon and thereby facilitate its insertion into the body through a percutaneous technique. The stylet is preferably formed of a conductive material or, alternatively, is formed of a material having a conductor embedded therein.

The distal tip of the IAB contains an electrode within a suitable insulating material formed of a plastic which is compatible with, and nontoxic to, the body. The distal end of the stylet is electrically connected to the electrode and the proximal end thereof extends through the balloon and catheter tube and is accessible at a location exterior to the body to facilitate electrical connection by means of a connector clip for coupling the electrode to monitoring and control circuitry. The stylet thus provides the dual functions of twisting and untwisting the balloon to facilitate percutaneous insertion and removal and balloon operation, respectively, and to provide means for electrical connection between an EKG electrode and monitoring and control circuitry. A small portion of the plastic material covering the electrode is removed, exposing the electrode to the body fluids (blood) which is sufficiently conductive to conduct the EKG signal from the heart through the blood and electrode and, hence, through the stylet to the monitoring and control instrumentation.

The EKG electrode carried by the IAB may be positioned either at the distal or proximal end of the balloon. The electrode next to the proximal end of the balloon may be coupled to the EKG electrode through a conductor embedded in the wall of the catheter. This arrangement may be used to eliminate the external electrode coupled to the chest of the patient.

BRIEF DESCRIPTION OF THE FIGURES AND OBJECTS OF THE INVENTION

It is, therefore, one object of the present invention to provide an IAB adapted for percutaneous insertion and having an EKG electrode and a stylet for twisting and untwisting the balloon and further for providing a high conductivity electrical path between the aforesaid EKG electrode and monitoring and control circuitry located external to the body.

Still another object of the present invention is to provide an IAB of the type described hereinabove and having a conductive stylet formed of a suitable metallic material.

Still another object of the present invention is to provide an IAB of the character described in which the stylet member is formed of an insulating material having a conductor embedded therein.

The above, as well as other objects of the present invention, will become apparent when reading the accompanying description and drawing in which:

FIGS. 6 and 7 show sectional views of still another preferred embodiment of the present invention.

FIG. 8 shows still another preferred embodiment of the present invention for coupling an electrode positioned adjacent to the proximal end of the balloon to EKG monitoring equipment.

FIG. 8a shows a detailed view of the electrical coupling between the electrode and the coupling conductor of FIG. 8.

FIG. 8b shows a detailed view of one preferred arrangement for coupling the proximal end of the coupling conductor FIG. 8 to EKG monitoring equipment.

FIG. 9 shows another manner for modifying the structure shown in FIG. 2 for eliminating spurious signals.

DETAILED DESCRIPTION OF THE INVENTION AND PREFERRED EMBODIMENTS THEREOF

Figure 1:
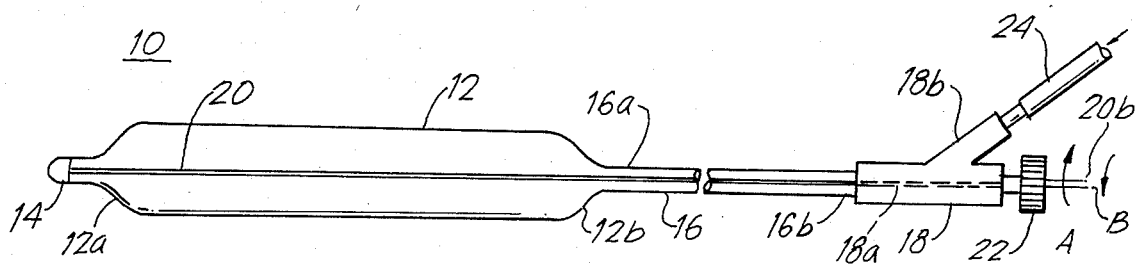
FIG. 1 shows a simplified plan view of an IAB embodying the principles of the present invention.

FIG. 1 shows an IAB 10 designed in accordance with the principles of the present invention and which is of the type described in the aforementioned copending application Ser. No. 253,680. IAB 10 is comprised of a balloon 12 having a tapered distal end 12a terminating in tip 14 and having a tapered proximal end 12b joined with and communicating with the distal ends 16a of catheter tube 16, whose proximal end 16b is joined with and communicates with coupling unit 18.

Coupling unit 18 is provided with a through bore 18a and a branch bore 18b. A stylet 20 has its distal end joined to or coupled with tip 14. Stylet 20 extends rearwardly through balloon 12 and catheter tube 16 and extends into the through bore 18a of coupling unit 18 and is joined with operating handle 22. The end 20b of stylet 20 extends beyond operating handle 22 for coupling to monitoring and control circuitry as will be more fully described. Branch bore 18b communicates with through-bore 18a and hence with catheter tube 16 for providing a path for receiving positive and negative pulsatile pressure pulses for respectively inflating and deflating ballon 12. An additional tube 24 may be provided for coupling branch bore 18b to the pressure operating source (not shown).

Figure 5:
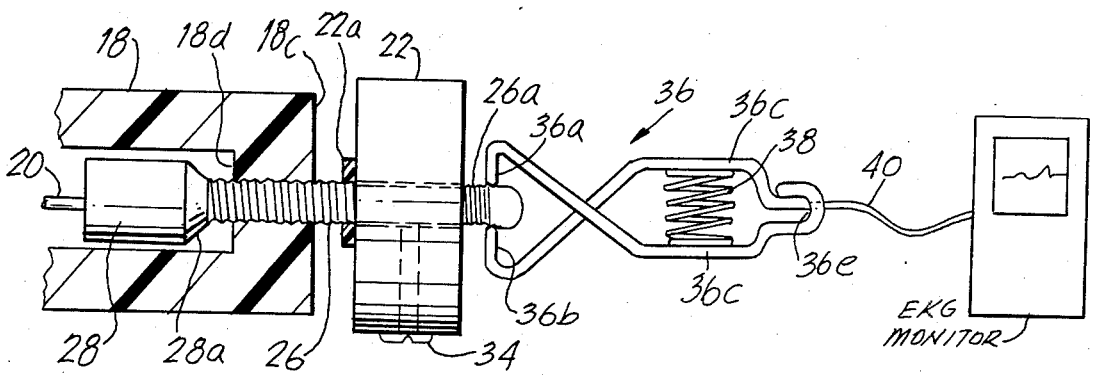
FIG. 5 shows the manner in which the stylet may be coupled to external monitoring and control circuitry.

Considering FIGS. 1 and 5 and assuming it is desired to prepare IAB 10 for insertion into the femoral artery, operating handle 22 is rotated in a first direction as shown by arrow A. Operating handle 22 is secured to threaded member 26 (by set screw 34) which in turn has an enlarged head portion 28 whose left-hand end is coupled to stylet 20. Rotation of operating handle 22 in the direction shown by arrow A causes member 26 and stylet 20 to rotate in the same direction, thereby causing the distal end 12a of balloon 12 to be twisted and, hence, wrapped about style 20 significantly reducing the outer diameter of the balloon when fully wrapped. The balloon 12 is preferably fully wrapped when control member 22 bears against the end 18c of coupling member 18. A gasket member 22a may provide an airtight seal between coupling member 18 and control member 22 when the balloon 12 is fully wrapped about stylet 20.

The balloon 12 is then inserted into the body preferably through a percutaneous technique. When properly inserted and positioned, the balloon 12 is untwisted by rotating operating member 22 in the reverse direction as shown by arrow B. The balloon 12 is untwisted when the diagonal shoulder 28a of enlarged head portion 28 bears against the interior wall 18d of coupling member 18, which also provides an air-tight seal.

Figure 2:
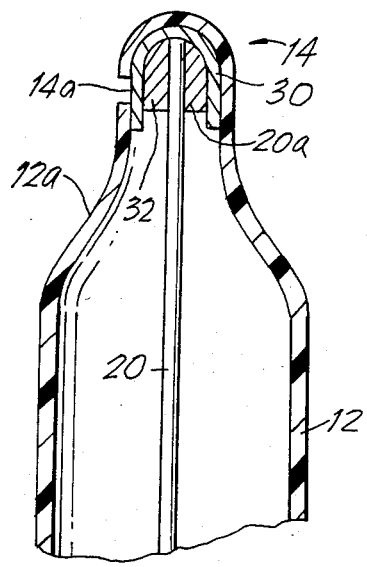
FIG. 2 shows an enlarged sectional view of the distal end portion of the IAB of FIG. 1.

As shown in FIG. 2, the distal end 20a of stylet 20 is electrically coupled to a cup-shaped electrode 30 embodied within the tip portion 14 of the IAB 10. The tapered portion 12a of balloon 12 is formed of an insulating plastic material, terminates in the tip portion 14 and subtantially completely covers electrode 30 except for a small portion 14a which exposes electrode 30. The distal end 20a of stylet 20 is preferably coupled to electrode 30 through suitable means such as, for example, a soldered joint 32. Any other suitable electrical and mechanical coupling arrangement may be employed.

Stylet 20 extends rearwardly, as was previously described, and is electrically connected to conductive member 26 which extends through operating handle 22, and is secured against movement or rotation relative to operating handle 22 by set screw 34. The right-hand end 26a of member 26 extends beyond operating handle 22 as shown, and is adapted for electrical coupling with electrical connector clip 36 whose free ends 36a and 36b of arms 36c and 36d respectively grip right-hand end 26a and maintain this firm gripping condition under the control of biasing spring 38. The right-hand of electrical connector clip 36 is provided with a cooperating hinge and electrical coupling arrangement 36e for electrical coupling with a wire 40 for connection with control and monitoring circuitry (not shown for purposes of simplicity), which may, for example, be a display monitor and control circuitry for recognizing the R wave of an EKG signal for controlling the timing of balloon pumping.

It should be understood that the remaining electrode for establishing a complete electrical path may be coupled in the conventional way, i.e. by mounting the remaining electrode (not shown) in the chest region of the patient and providing conductor means between the remaining electrode and the monitoring and control circuitry.

Figure 2A:
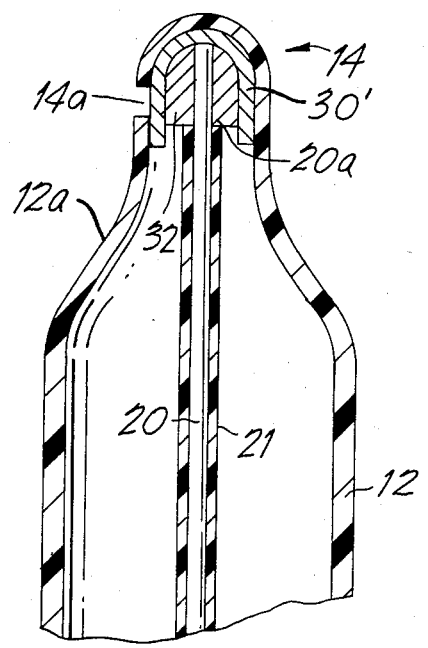
FIG. 2a shows one manner for modifying the structure shown in FIG. 2 for eliminating spurious signals.

FIG. 2a and FIG. 9 show a slightly modified arrangement 10' for that shown in FIG. 2 wherein stylet 20 is covered with an insulating film 21 to prevent a "weak" electrical signal derived from distal end 14 and coupled from electrode 30' to stylet 20 from picking up interference from conductive fluids which may be present within balloon 12 and/or catheter 16. Such fluids are transmitted through the balloon membrane 12 from the patient by a "reverse osmosis" process. These fluids are often conductive and generate a signal as they are sloshed around within the interior of balloon 12 and/or catheter 16, due either to the expansion and/or collapse of the balloon or the movement of the gases causes inflation and deflation of the balloon.

Figure 3:
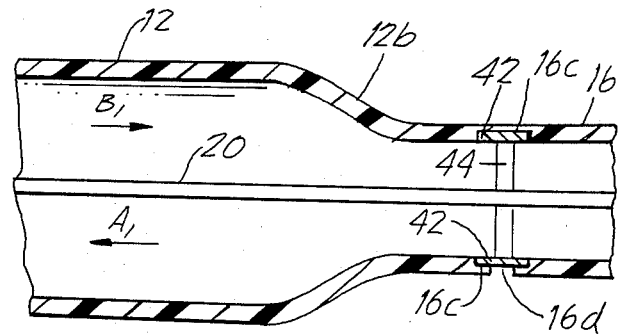
FIG. 3 shows a sectional view of another alternative embodiment of the present invention.
Figure 4:
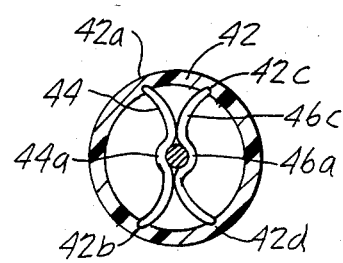
FIG. 4 shows an end view of the EKG electrode employed in the alternative embodiment of FIG. 3.

FIGS. 3 and 4 show an alternative embodiment of the present invention in which the electrode may be arranged in the region of the proximal end 12b of balloon 12. As shown in FIG. 3, the electrode 42 comprises an annular conductive ring embedded within the catheter tube 16 which may be provided with a groove 16c about its interior periphery for receiving and positioning electrode 42. A pair of arcuate-shaped conductive leaf spring members 44 and 46 have their ends arranged within recesses 42a through 42d arranged at spaced intervals about the inner periphery of electrode 42. Each of the conductive leaf spring members 44 and 46 is provided with a semi-circular shaped central portion 44a, 46a which semi-circular shaped portions cooperate to form a circular-shaped portion for receiving stylet 20 which makes wiping engagement with the conductive leaf spring members 44 and 46 while, at the same time, being capable of rotation about its longitudinal axis and movement in the axial direction either to the left or to the right, as shown by arrows A1 and B1 due to rotation of operating member 22 and hence threaded member 26 in the rotational directions A and B respectively.

Thus, an electrically conductive path is provided between stylet 20 and electrode 42 through conductive leaf springs 44 and 46. Similar to the embodiment shown in FIG. 2, a portion 16d of catheter tube 16 is removed to expose a portion of electrode 42. Electrical connection between electrode 42 and stylet 20 is established in the same manner as is shown in FIG. 5 wherein stylet 20 is electrically connected, preferably by soldering or similar mechanical and electrical joining technique, to head portion 28 which may be coupled to external monitoring and control circuitry through electrical coupling clip 36 and electrical wire 40.

FIGS. 6 and 7 show another alternative embodiment 50 of the present invention wherein like elements as between the previous figures and FIGS. 6 and 7 are designated by like numerals. In place of stylet 20, there is provided a hollow, flexible, elongated tube 52 of a diameter which is appreciably smaller than the inner diameter of catheter tube 16. To prevent torsional forces from twisting hollow tube 52, a pair of wires 54 and 56 embedded within the wall of tube 52 are arranged in helical patterns of first and second opposite senses. At least one of said wires (or both if desired) are connected to electrode 30 at the distal end 52a of tube 52, establishing an electrical path between EKG electrode 30 and one or both of said conductive wires 54 and 56. Opening 14a in the insulation layer covering electrode 30 establishes electrical contact with the blood in the aortic arch.

The proximal end 52b of tube 52 is coupled to one end of enlarged member 28 and at least one of the proximal ends of wires 54 and 56 are electrically connected to conductive member 28, thus establishing an electrical path from electrode 30 through one or both wires 54 and 56 to member 26 whose right-hand end 26a extends beyond the right-hand end of operating knob 22 for coupling with an electrical connecting clip such as the clip assembly 36 shown in FIG. 5.

Rotation of operating knob 22 serves to rotate elongated tube 52 for twisting and wrapping balloon 12 about the stylet member 52. The balloon is now ready for insertion, preferably through a percutaneous technique.

After insertion and proper placement of the balloon within the aortic arch, operating knob 22 is rotated in the reverse direction to untwist balloon 12 in readiness for assisting the heart in the pumping of blood. Monitoring and control of the heart and the pumping function is established by coupling electrode 30 through conductors 54 (and/or 56) to monitoring and control circuitry in the same manner as was previously described with respect to the embodiments of FIGS. 1 through 5.

As an additional capability, member 26 is provided with a through bore 26b which communicates with the hollow interior of tube 52 to permit pressure monitoring, insertion of a separate independent probe and for other monitoring or treatment purposes. In order to accomplish this function, tip 14 is provided with an open end 14b with the insulating cover communicating with the distal end of tube 52, as shown best in FIG. 12, providing fluid-tight isolation between the interior of tube 52 and the interior of balloon 12.

The electrode 42 shown in FIG. 3 may be coupled to EKG monitoring apparatus through an arrangement different from that shown in FIG. 3 and, more specifically, as shown in FIGS. 8 through 8b. Although electrode 42 is shown arranged adjacent to the proximal tapered end 12b of balloon 12, and surrounding that portion of catheter tube 16 adjacent to tapered end 12b, the catheter 16 is provided with an electrical conductor 17 embodied within the wall of catheter 16 and extending along the length of catheter 16 and preferably substantially parallel to the longitudinal axis of catheter 16. A portion of the catheter wall 16 is removed to form a wedge-shaped groove 19 through which conductor 17 extends. The wedge-shaped groove 19 is filled with a conductive epoxy 21 which fills the wedge-shaped groove 19 and electrically couples electrode 42 to conductor 17. Electrode 42 may be exposed or covered with an insulation layer, as shown in FIG. 3.

FIG. 8b shows the proximal end of catheter 16 extending into the hollow interior 23a of a coupling member 23, having a shallow peripheral recess 23b for receiving a cylindrical-shaped conductive member 25. A radially aligned electrode 27 extends through the wall of coupling 23 with its lower end 27a electrically connected to conductive cylinder 25 and so that its upper end 27a extends beyond the outer periphery 23c of the coupling 23, and is available for electrical connection to an EKG monitoring device, for example.

A wedge-shaped groove 16e is formed in catheter tube 16 and is of a depth sufficient to expose at least a portion of conductor 17. The wedge-shaped groove 16e is filled with a conductive epoxy 29, which electrically couples conductor 17 to conductive cylinder 25. The end 27a of electrode 27 is also preferably coupled to conductive ring 25 by a layer of conductive epoxy 31 positioned between end 27a of electrode 27 and the exterior periphery of conductive cylinder 25.

Thus, as can be seen from FIGS. 8 through 8b, the continuous conductive path extends from electrode 42 through conductor 17 embedded within the wall of catheter 16, conductive epoxy 29, conductive cylinder 25, and conductive epoxy 31 to electrode 27 which may be coupled to monitoring equipment such as an EKG monitor.

Using the arrangement shown in FIGS. 8 through 8b, the stylet 20 may be utilized to couple an electrode arranged in the balloon tip, as shown in FIG. 2, in which the end 20a of stylet 20 is electrically coupled to conductive electrode 30. By incorporating the electrode arrangements shown in FIGS. 2 and 8 into an intra-aortic balloon assembly, it is possible to provide a pair of EKG electrodes arranged within the body of the patient, and thereby totally eliminate the need for an external EKG electrode, which is necessary in the event that only one of the techniques shown in FIGS. 2 and 8 is incorporated into an intra-aortic balloon assembly.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. An intra-aortic balloon assembly comprising:
an inflatable balloon formed of a nonstretchable plastic material and having a distal end terminating in a tip and having an open proximal end;
an elongated catheter tube having an open distal end communicating with and air-tightly joined to the open proximal end of said balloon, and having a proximal end for receiving positive and negative pressure pulses for selectively inflating and deflating said balloon;
a flexible elongated conductive stylet extending from said balloon distal end and through said balloon and said catheter tube and accessible at the proximal end of said catheter tube and being rotatable about its longitudinal axis to rotate said tip and said balloon to wrap said balloon about said stylet when rotated in a first direction and to unwrap said balloon from said stylet when rotated in the opposite direction;
said tip containing a conductive electrode, the distal end of said stylet being electrically connected to said electrode;
said tip including insulation means covering said electrode and having at least a portion thereof removed to expose a portion of the surface of said electrode;
means coupled to the proximal end of said stylet for coupling the electrical condition at said electrode to an output utilization device.

2. The intra-aortic balloon assembly of claim 1, wherein said stylet is an elongated conductive wire.

3. The intra-aortic balloon assembly of claim 1, wherein said stylet is an elongated hollow tubular conductive member.

4. The intra-aortic balloon assembly of claim 1, wherein said stylet is an elongated hollow tubular member formed of an insulating material and having a conductive wire embedded in the wall thereof;
one end of said wire being connected to the electrode arranged in said tip and the other end being electrically connected to said coupling means.

5. The intra-aortic balloon assembly of claim 4, wherein said wire is arranged in a helical fashion in the wall of said tubular member.

6. The intra-aortic balloon assembly of claim 4, wherein said wire is substantially parallel to the longitudinal axis of said hollow tubular member.

7. The intra-aortic balloon assembly of claim 1, wherein said stylet is an elongated conductive wire covered with a film of insulation material to insulate said wire from conductive fluids, which may be present within the interior of the balloon and catheter tube of said intra-aortic balloon assembly.

8. The intra-aortic balloon assembly of claim 1, wherein said coupling means is further characterized as being fixedly mounted upon the proximal end of said catheter tube and having manually rotatable means rotatable relative to said coupling means and being connected to the proximal end of said stylet for selectively rotating said stylet in a first and second direction;
said manually rotatable means including a conductive member having a first end extending into said coupling means and joined to the proximal end of said stylet, and having a second end extending outwardly from said coupling means, and having at least a portion thereof exposed for coupling with an external utilization means.

9. The intra-aortic balloon assembly of claim 8, wherein said manually rotatable means includes a knob formed of an insulating material;
said conductive member extending through said knob and means on said knob for securing said knob to said conductive member.

10. The intra-aortic balloon assembly of claim 9, wherein said coupling means has a threaded opening for receiving said conductive member;
said conductive member threadedly engaging said threaded opening.

11. An intra-aortic balloon assembly comprising:
an inflatable balloon formed of a nonstretchable plastic material and having a distal end terminating in a tip and having an open proximal end;
an elongated catheter tube having an open distal end communicating with and air-tightly joined to the open proximal end of said balloon, and having a proximal end for receiving positive and negative pressure pulses for selectively inflating and deflating said balloon;
a flexible elongated conductive stylet extending from said balloon distal end through said balloon and said catheter tube and accessible at the proximal end of said catheter tube and being rotatable about its longitudinal axis to rotate said tip and said balloon to wrap said balloon about said stylet when rotated in a first direction and to unwrap said balloon from said stylet when rotated in the opposite direction;
an electrode encircling a portion of the catheter tube at a location adjacent the proximal end of the balloon and means arranged within said electrode for electrically connecting said electrode to said stylet;
insulation means covering said electrode having at least a portion thereof removed to expose a portion of the surface of said electrode;
means coupled to the proximal end of said stylet for coupling the electrical condition at said electrode to an output utilization device.

12. The intra-aortic balloon assembly of claim 11, wherein said electrode is a cylindrical-shaped conductive shell;
said connecting means comprising resilient conductive biasing members joined to said conductive shell and wipingly engaging said stylet for establishing an electrical path from said electrode through said biasing members to said stylet.

13. The intra-aortic balloon assembly of claim 11, wherein said electrode is a cylindrical-shaped conductive shell;
said connecting means comprising a pair of arcuate-shaped resilient conductive members having their outer ends joined to the inner periphery of said conductive shell;
the central portion of said arcuate-shaped members having a semi-circular shaped configuration and being arranged so that said semi-circular portions cooperatively define a substantially circular-shaped opening through which the stylet extends, said arcuate-shaped members making continuous wiping engagement with said stylet to establish an electrical path between said stylet and said electrode.

14. The intra-aortic balloon assembly of claim 13, wherein said catheter tube substantially completely covers said electrode to define said insulation means;

a portion of said catheter tube wall being removed to expose a portion of the conductive shell positioned therebeneath.

15. An intra-aortic balloon assembly comprising:
an inflatable balloon formed of a non-stretchable plastic material and having a distal end terminating in a tip and having an open proximal end;
an elongated catheter tube having an open distal end communicating with and air-tightly joined to the open proximal end of said balloon, and having a proximal end for receiving positive and negative pressure pulses for selectively inflating and deflating said balloon;
a flexible elongated conductive stylet extending from said balloon distal end through said balloon and said catheter tube and accessible at the proximal end of said catheter tube and being rotatable about its longitudinal axis to rotate said tip and said balloon to wrap said balloon about said stylet when rotated in a first direction and to unwrap said balloon from said stylet when rotated in the opposite direction;
said tip containing a first conductive electrode, the distal end of said stylet being electrically connected to said first electrode;
said tip including insulation means covering said first electrode having at least a portion thereof removed to expose a portion of the surface of said first electrode;
a second electrode arranged along said catheter tube at a location adjacent to the proximal end of said balloon;
first coupling means arranged at the proximal end of said stylet for coupling the electrical condition at said first electrode to an output utilization device;
a conductor embedded in the wall of said catheter tube having a distal end adjacent to said second electrode and a proximal end arranged adjacent to the proximal end of said catheter tube;
second coupling means for electrically coupling said second electrode to the distal end of said conductor;
a third coupling electrode; and
third coupling means for electrically connecting the proximal end of said conductor to said third electrode.

16. The intra-aortic balloon assembly of claim 15, wherein said catheter tube is provided with a groove along its exterior periphery and extending into the catheter tube wall to a depth sufficient to expose the distal end of the conductor; and
said second coupling means comprising conductive epoxy means being provided in said groove and engaging said conductor and said second electrode for establishing an electrical path therebetween.

17. The intra-aortic balloon assembly of claim 15, wherein the exterior periphery of said catheter tube is provided with a groove, said groove having a depth sufficient to expose the proximal end of the conductor; and
said third coupling means including conductive epoxy means provided in said groove for electrically connecting said conductor and said third coupling electrode.

18. The intra-aortic balloon assembly of claim 15, wherein said stylet is a tubular member.

19. The intra-aortic balloon assembly of claim 18, wherein said tubular member is conductive.

20. The intra-aortic balloon assembly of claim 18, wherein said tubular member is formed of a plastic material having a conductor embedded in the wall of said tubular member;
said tubular member conductor being electrically connected between said first electrode in said tip and said first coupling means.

21. An intra-aortic balloon assembly comprising:
an inflatable balloon formed of a nonstretchable plastic material and having a distal end terminating in a tip and having an open proximal end;
an elongated catheter tube having an open distal end communicating with and air-tightly joined to the open proximal end of said balloon, and having a proximal end for receiving positive and negative pressure pulses for selectively inflating and deflating said balloon;
a flexible elongated conductive stylet extending from said balloon distal end through said balloon and said catheter tube and accessible at the proximal end of said catheter tube, and being rotatable about its longitudinal axis to rotate said tip and said balloon to wrap said balloon about said stylet when rotated in a first direction, and to unwrap said balloon from said stylet when rotated in the opposite direction;
said tip containing a conductive electrode electrically connected to the distal end of said stylet, said tip having at least a portion thereof removed to expose a portion of the surface of said electrode;
means coupled to the proximal end of said stylet for coupling the electrical condition at said electrode to an output utilization device;
a conductor embedded in the wall of said catheter tube;
a second electrode arranged on said catheter tube adjacent to said balloon;
conductive epoxy means electrically connecting said conductor to said second electrode;
a coupling member joined to the proximal end of said catheter tube;
said coupling member having a connecting electrode;
conductive epoxy means electrically connecting said conductor to said connecting electrode.

* * * * *